United States Patent
Lin

(10) Patent No.: US 9,500,792 B2
(45) Date of Patent: Nov. 22, 2016

(54) METHOD FOR MANUFACTURING ARTIFICIAL SMOLDERING SCENT-STICK

(71) Applicant: HON HAI PRECISION INDUSTRY CO., LTD., New Taipei (TW)

(72) Inventor: Chen-Han Lin, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 187 days.

(21) Appl. No.: 14/265,341

(22) Filed: Apr. 29, 2014

(65) Prior Publication Data

US 2014/0322454 A1 Oct. 30, 2014

(30) Foreign Application Priority Data

Apr. 30, 2013 (TW) ................................. 102115350

(51) Int. Cl.
*F21V 8/00* (2006.01)

(52) U.S. Cl.
CPC .......... *G02B 6/0008* (2013.01); *A61L 2209/12* (2013.01)

(58) Field of Classification Search
CPC ......................... G02B 6/0008; A61L 2209/12
USPC ........................................................ 427/516
See application file for complete search history.

(56) References Cited

U.S. PATENT DOCUMENTS

2014/0119047 A1* 5/2014 Lee ...................... G02B 6/0001
362/562

* cited by examiner

*Primary Examiner* — Robert S Walters, Jr.
(74) *Attorney, Agent, or Firm* — Zhigang Ma

(57) ABSTRACT

A method for manufacturing the hemispherical light emitting portion of an artificial smoldering scent-stick comprises the steps of providing a light guide pipe and a light emitting element. The light guide pipe includes a bottom end and a top end opposite to the bottom portion. The light emitting element is fixed on the bottom end. A colloid is dripped on an end face of the top end and the colloid cured, to obtain the shape of the required light-emitting portion.

8 Claims, 2 Drawing Sheets

METHOD FOR MANUFACTURING ARTIFICIAL SMOLDERING SCENT-STICK

FIELD

The present disclosure relates to a method for manufacture of an artificial smoldering scent-stick.

BACKGROUND

An artificial smoldering scent-stick includes a hemispherical head. The hemispherical head can emit red light. A method for manufacturing this component is grinding and polishing the hemispherical head but this way is time-consuming.

DETAILED DESCRIPTION

Figure 1:
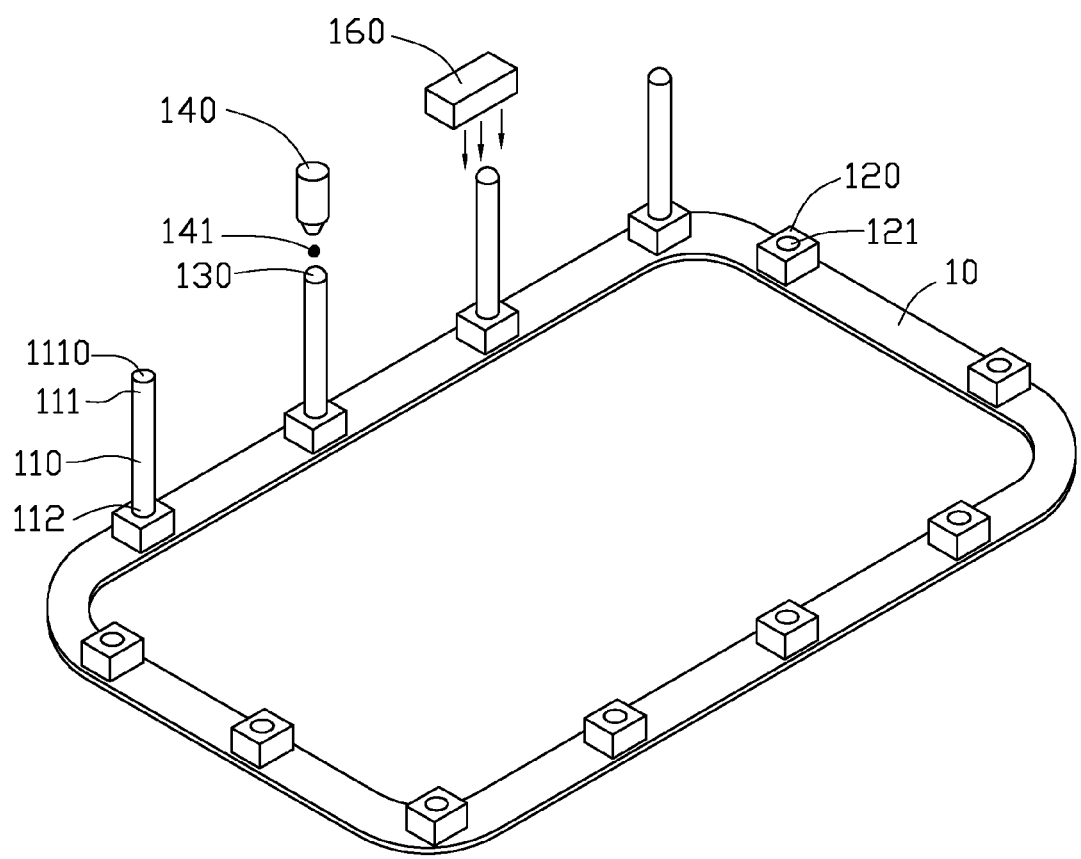
FIG. 1 is a flow diagram of a method for manufacturing the light-emitting portion of an artificial smoldering scent-stick.

The disclosure is illustrated by way of example and not by way of limitation in the figures of the accompanying drawings in which like reference numerals indicate similar elements. It should be noted that references to "an" or "one" embodiment in this disclosure are not necessarily to the same embodiment, and such references mean "at least one." The references "a plurality of" and "a number of" mean "at least two."

Figure 2:
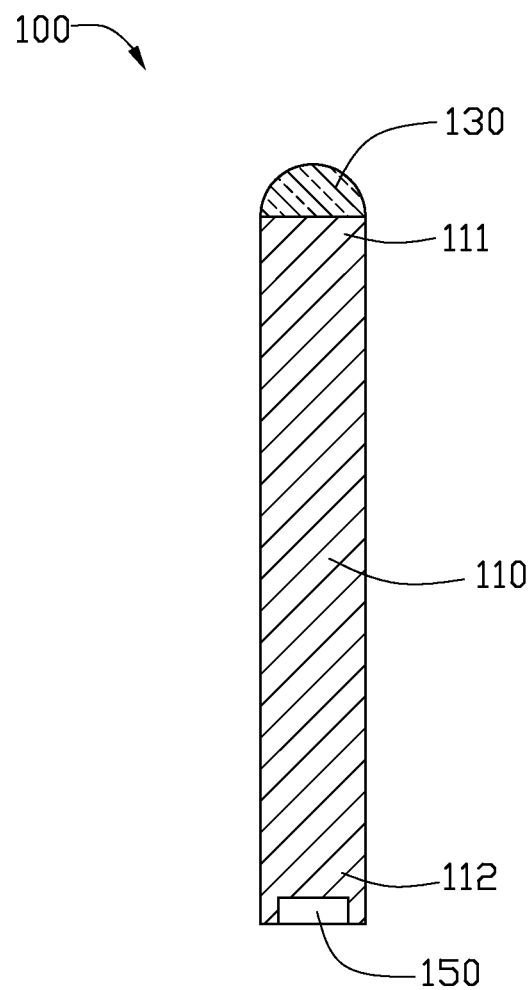
FIG. 2 is a schematic view of the light-emitting portion of FIG. 1.

FIGS. 1 to 2 illustrate a method for manufacturing an artificial smoldering scent-stick 100 according to an embodiment, comprising following steps.

First, a conveyor 10 is provided. The conveyor 10 includes multiple positioning members 120. Each positioning member 120 includes a positioning hole 121.

In this embodiment, the positioning hole 121 is a cylindrical cavity. The conveyor 10 is driven to move by a driver (not shown).

Second, a light guide pipe 110 and a light emitting element 150 are provided. The light guide pipe 110 includes a bottom end 112 and a top end 111 opposite to the bottom end 112. The bottom end 112 is received in one of the positioning holes 121. The light guide pipe 110 is driven to move along a transporting direction of the conveyor 10.

The light guide pipe 110 is cylindrical. An outer of the light guide pipe 121 is equal to or slightly less than a diameter of the positioning hole 121, thus the light guide pipe 110 can have a clearance fit in the inner wall of the positioning hole 121. The light emitting element 150 is fixed on the bottom end 112 of the light guide pipe 110. The light emitting element 150 is a light-emitting diode. The light guide pipe 110 is made of polymethyl methacrylate. The light emitting element 150 emits light. The light guide pipe 110 conducts the light.

Third, a robot dispenser 140 is provided. The robot dispenser 140 contains colloid 141. The robot dispenser 140 is positioned above the conveyor 10. When the light guide pipe 110 is moving under the dispensing robot dispenser 140, the colloid 141 is dripped on an end face 1110 of the top end 111.

The colloid 141 is transparent material. In this embodiment, the colloid 141 is ultraviolet curing adhesive. Because of its own viscosity and effects of gravity, the colloid 141 forms a hemispherical body on the end surface 1110.

Forth, a curing machine 160 is provided. The curing machine 160 cures the colloid 141. In this embodiment, the curing machine 160 is an ultraviolet irradiation device 160. The transparent element 130 is cured by the ultraviolet irradiation device 160, and thereby the light emitting portion is obtained.

In another embodiment, the transparent element 130 can also be cured by heat.

In another embodiment, the transparent element 130 can also be positioned and dropped by another kind of transfer device.

Referring to FIG. 2, the artificial smoldering scent-stick 100 includes a light guide pipe 110, a light emitting element 150, and a transparent element 130. The light guide pipe 110 includes a bottom end 112 and a top end 111 opposite to the bottom end 112. The light emitting element 150 is fixed on the bottom portion 112 of the light guide pipe 110. The transparent element 130 is adhered to the top end 111 of the light guide pipe 110. The transparent element 130 is in the shape of a hemisphere. In this embodiment, the transparent element 130 is made of UV curing adhesive.

The light emitting element 150 is a light-emitting diode. In this embodiment, the light emitting element 150 emits red light, so the color of the transparent element 130 is similar to the color of smoldering material.

It is to be understood, however, that even though numerous characteristics and advantages of the present embodiments have been set forth in the foregoing description, together with details of the structures and functions of the embodiments, the disclosure is illustrative only, and changes may be made in detail, especially in matters of shape, size, and arrangement of parts within the principles of the disclosure to the full extent indicated by the broad general meaning of the terms in which the appended claims are expressed.

What is claimed is:

1. A method for manufacturing an artificial smoldering scent-stick, comprising:
    providing a light guide pipe and a light emitting element, the light guide pipe comprising a bottom end and a top end opposite to the bottom end, the light emitting element fixed on the bottom end of the light guide pipe;
    providing a colloid, dripping the colloid on an end face of the top end;
    curing the colloid, thereby obtaining the artificial smoldering scent-stick.

2. The method of claim 1, wherein the light guide pipe is arranged on a conveyor, the conveyor comprising a plurality of positioning members, the light guide pipe arranged on the positioning member, the light guide pipe is driven to move along a transporting direction of the conveyor.

3. The method of claim 2, wherein each positioning member includes a positioning hole, the bottom end of the light guide pipe is received in one of the positioning holes.

4. The method of claim 3, wherein the light guide pipe is cylindrical, an outer diameter of the light guide pipe is equal to or slightly less than a diameter of the positioning hole, thus the light guide pipe is a clearance fit in an inner wall of the positioning hole.

5. The method of claim 2, wherein the step of dripping the colloid on the end face of the top end comprises:
    disposing a robot dispenser above the conveyor, the robot dispenser containing the colloid;
    moving the light guide pipe to be under the robot dispenser by the conveyor;

dripping the colloid on the end face of the top end by the robot dispenser.

6. The method of claim 1, wherein the light guide pipe is made of polymethyl methacrylate material.

7. The method of claim 1, wherein the colloid is cured by heat or by ultraviolet radiation.

8. The method of claim 7, wherein the cured colloid forms a transparent element on the end face of the top end, and the transparent element is in the shape of a hemisphere.

\* \* \* \* \*